United States Patent [19]

Sugisaki

[11] Patent Number: 5,863,582
[45] Date of Patent: Jan. 26, 1999

[54] POWDERED VEGETABLE AND/OR FRUIT JUICE AND MANUFACTURING PROCESS THEREOF

[75] Inventor: Takashi Sugisaki, Kawaguchi, Japan

[73] Assignee: M-P-G Co., Ltd., Tokyo, Japan

[21] Appl. No.: 873,195

[22] Filed: Jun. 11, 1997

[30] Foreign Application Priority Data

Feb. 17, 1997 [JP] Japan ................................. 9-048383

[51] Int. Cl.[6] ............................ A23B 7/024; A23L 1/015
[52] U.S. Cl. ............................ 426/271; 426/66; 426/384; 426/385; 426/455; 426/456; 426/599; 426/615; 426/640; 426/648; 426/650
[58] Field of Search ............................ 426/271, 66, 615, 426/640, 648, 455, 456, 599, 650, 384, 385

[56] References Cited

U.S. PATENT DOCUMENTS 5,407,696    4/1995    Hagiwara ................................. 426/599

*Primary Examiner*—Helen Pratt
*Attorney, Agent, or Firm*—Michael D. Bednarek; Kilpatrick Stockton LLP

[57] ABSTRACT

Vegetables or macerated vegetables were washed with water passed through ion-exchange resins capable of removing $NO_3^-$ and $NO_2^-$ ions to remove nitrate nitrogen harmful to human body, then pulverized by freeze-drying. Then, powdered vegetable juice is obtained by adding components effective for healthy life thereto.

9 Claims, No Drawings

POWDERED VEGETABLE AND/OR FRUIT JUICE AND MANUFACTURING PROCESS THEREOF

FIELD OF THE INVENTION

The present invention relates to powdered vegetable juice and manufacturing process thereof, wherein said powdered vegetable juice is free from nitrate nitrogen harmful to human body and is added with components effective to maintaining healthy life such as the prevention of senescence and the reinforcement of blood vessels.

BACKGROUND TO THE INVENTION

Recently, water pollution with nitrate nitrogen is becoming serious social concern year by year together with ground water contamination with organochlorine compounds such as trichloroethylene. Nitrate nitrogen which are contaminants of said ground water and also derive from nitrogen fertilizers and pesticides also exist as nitrates and nitrites in organisms.

That is, organic nitrogen contained in debris will penetrate into soil, become decomposed into ammonia nitrogen therein and subsequently oxidized to nitrate through nitrite.

Therefore, nitrate nitrogen is widely distributing in many plants, particularly in vegetables since nitrate nitrogen in ground water, although mainly exist as nitrates in ground water, after easily translocated together with ground water, or nitrate nitrogen derived from fertilizers or pesticides again are taken up by plants and incorporated into organisms.

Toxicity of said nitrates to human is believed due to reduction of nitrate by microorganisms in the body to nitrites. It is well known that said nitrites not only oxidizes hemoglobin having an important rule as an oxygen transporter in blood to methemoglobin which lacks the oxygen transport ability, resulting in oxygen deficiency in various organs, but also causes adverse effect such as senescence of blood vessels. Further, it is known that nitrites reacts in stomach with secondary amines, non-carcinogens, to form nitrosoamines, carcinogens.

As ordinary methods to obtain powdered vegetable juice or powdered vegetables as food supplements, several methods are proposed; a method to freeze-dry fresh vegetables followed by pulverization using a mill, a method to dry fresh vegetables using a dryer followed by pulverization using a mill, another method to squeeze fresh vegetables avoiding decomposition of components, freeze-drying the resulting liquid followed by further pulverization using a mill. But, there are no methods referring nitrate nitrogen harmful to human body, contained in or deposited on vegetables.

SUMMARY OF THE INVENTION

The object of the present invention is to provide powdered vegetable juice and manufacturing process thereof, wherein said powdered vegetable juice is free from nitrate nitrogen which are harmful to human body and contained in or deposited on vegetables and is added with components effective to maintaining healthy life.

In order to obtain powdered vegetable juice implementing said object, in the manufacturing process according to the present invention, vegetables, preferably macerated vegetables are washed with water passed through an ion-exchange resin capable of removing $NO_3$- and $NO_2$-ions to remove nitrate nitrogen, and subsequently freeze-dried and pulverized. Resulting powdered vegetable juice is supplemented with components effective to maintain healthy life such as blood vessel reinforcers and various vitamins.

Further, powdered vegetable juice according to the present invention can be mainly packed into an air-tight stick-type container containing the volume sufficient to one cup of glass or into other types of containers and used for beverage after dissolved in water when necessary or used as a supplement for various foods, infant food and hospital diet. It is also effective to solve the deviated food habit, particularly vegetable dislike.

GENERAL DESCRIPTION OF THE INVENTION

The present invention will be further described in detail. Vegetables used in the present invention are celery, *komatsuna* (*Brassica campestris, rapifera* group), *chingensai* (*B. campestris, chinensis* group), Garland chrysanthemum, parsley, lettuce, spinach, asparagus, carrot, Welsh onion, Chinese cabbage, cabbage, Japanese hornwort, Japanese mugwort, tomato and other vegetables including fruits such as apple.

The ion-exchange resins used to remove nitrate nitrogen are anion-exchange resins capable of removing $NO_3$- and $NO_2$-ions, for example a strong basic ion-exchange resin (Cl- ion form).

Then, methods and results of nitrate nitrogen removal tests will be presented.

First, method and results of nitrate nitrogen removal test (1) used to remove nitrate nitrogen deposition on the surface of vegetables will be explained.

Nitrate nitrogen removal test (1)

(a) One hundreds grams each of seven different vegetables (celery, *komatsuna, chingensai*, Garland chrysanthemum, parsley, lettuce and spinach) were weighed out, and equally divided into two portions.

(b) Seven containers filled with 6 liters of tap water treated with said ion-exchange resin (hereinafter referred to "purified water")and seven containers filled with 6 liters of untreated tap water (hereinafter referred to "tap water") were prepared.

(c) Each of said fresh vegetable samples was thoroughly washed by hand in each container for 3 minutes.

(d) After removed the fresh vegetable sample from the container, the amount (mg/liter) of nitrate nitrogen in washing in the container was determined using a pack-test equipment for water quality test (Kyouritsu Rika K. K.).

(e) Above procedures (a) to (d) were repeated until the amount of nitrate nitrogen in said washing becomes 0.

Results obtained from the nitrate nitrogen removal test (1) are presented in Table 1 below.

TABLE 1

| Vegetables | | No. of washing | | | | | | | | | |
|---|---|---|---|---|---|---|---|---|---|---|---|
| | | 1 | 2 | 3 | 4 | 5 | 6 | 7 | 8 | 9 | 10 |
| celery | purified water | 2.3 | 1.15 | 1.15 | 1.15 | 1.15 | 1.15 | 1.15 | 0.46 | 0.23 | 0 |
| komatsuna | purified water | 2.3 | 2.3 | 2.3 | 2.3 | 2.3 | 2.3 | 1.15 | 0.46 | 0 | |
| chingensai | purified water | 1.15 | 1.15 | 0.46 | 0.46 | 0.46 | 0.23 | 0.23 | 0 | | |
| Garland chrysanthemum | purified water | 2.3 | 1.15 | 1.15 | 1.15 | 1.15 | 1.15 | 1.15 | 0.46 | 0.23 | 0 |
| parsley | purified water | 0.46 | 0.23 | 0 | | | | | | | |
| lettuce | purified water | 0.46 | 0.46 | 0.46 | 0.46 | 0.23 | 0.23 | 0 | | | |
| spinach | purified water | 1.15 | 1.15 | 1.15 | 1.15 | 0.46 | 0.46 | 0.46 | 0.23 | 0.23 | 0 |

Amount of nitrate nitrogen (mg/litter)

As obvious from Table 1, when washing with purified water was repeated, washing efficiency increased every time washing is repeated and the amount of nitrate nitrogen in said washing became by 3 to 10 times washing depending on vegetable used. Therefore, it was confirmed that nitrate nitrogen deposited on fresh vegetables were completely removed. This was true for dried vegetables separately tested.

On the other hand, in case washing was made with tap water, although it was expected that a small amount of nitrate nitrogen might be released into washing at least first wash, measurable amount of nitrate nitrogen was not detected probably because the level was too low to detect by said determination method. Even though said washing was repeated further, presence of nitrate nitrogen in washing could not be confirmed. Therefore, it was considered that nitrate nitrogen were not removed from said fresh vegetables.

Then, method and results of nitrate nitrogen removal test (2) used to remove nitrate nitrogen deposited on the surface of and contained in vegetables will be explained.

Nitrate nitrogen removal test (2)

(a) One hundreds grams each of 14 different vegetables (asparagus, tomato, carrot, apple, Welsh onion, celery, *komatsuna, chingensai*, Garland chrysanthemum, parsley, lettuce, spinach, Chinese cabbage and Japanese hornwort) were weighed out.

(b) Each of said vegetable samples was cut into a square pieces of about 1×1 cm and prepared in almost crushed state in a mortar carefully to avoid decomposition of nutrients.

(c) Then, 0.2 ml of the resulting extract of each vegetable sample was diluted with said purified water to 100 times. The concentration of nitrate nitrogen in this diluted extract was determined spectroscopically using a simplified reflectance spectrometer RQ Flex Canto Chemical Co., Ltd.); the test paper was dipped into the diluted extract for 2 seconds, excess water on the test paper was removed, then the paper was inserted in the equipment.

(d) Extracted residue (mainly fiber components) remained after extract was separated according to this method was diluted again with purified water to 100 times and the concentration of nitrate nitrogen was determined using said RQ Flex in similar way as above to confirm the amount of nitrate nitrogen remaining in the extracted residue of each vegetable sample.

Results of said nitrate nitrogen removal test (2) are presented in Table 2 below.

TABLE 2

| | Concentration (mg/L) of nitrate nitrogens | | | | |
|---|---|---|---|---|---|
| Vegetables | Extract | Residue | Vegetables | Extract | Residue |
| celery | 751 | N.D. | asparagus | 1 | N.D. |
| komatsuna | 1066 | N.D. | tomato | 9 | N.D. |
| chingensai | 744 | N.D. | carrot | 828 | N.D. |
| Garland chrysanthemum | 633 | N.D. | Welsh onion | 598 | N.D. |
| parsley | 874 | N.D. | Japanese hornwort | 1311 | N.D. |
| lettuce | 460 | N.D. | apple | 13 | N.D. |
| spinach | 989 | N.D. | Chinese cabbage | 598 | N.D. |

N.D.: not detected (<0.3 mg/L)

As obvious from Table 2, nitrate nitrogen could be detected from each of said fresh vegetable extracts; 460 mg/liter from lettuce extract and relatively high level of 1311 mg/liter from Japanese hornwort, but it was confirmed that the level of nitrate nitrogen in the purified water extracted residue of each vegetable sample was only trace and below the detection limit of 0.3 mg/liter.

As mentioned above, the manufacturing process of powdered vegetable juice including the steps to remove nitrate nitrogen on the surface of vegetables according to said nitrate nitrogen removal test (1) followed by pulverization using a freeze-dryer commercially available, then adding various components effective for maintaining a healthy life such as blood vessel reinforcers and various vitamins can provide powdered vegetable juice containing significantly low level of nitrate nitrogen compared to any of the ordinary methods.

However, nitrate nitrogen exist also in vegetable tissue. Therefore, more preferably, vegetable is cut finely as much as possible to prepare macerated vegetable, prepared to almost crushed state, washed with purified water according to said nitrate nitrogen removal test (2), pulverized using a freeze-dryer, then powdered vegetable juice is constituted by adding with various components effective for maintaining healthy life such as blood vessel reinforcers and various vitamins.

As blood vessel reinforcers, for example, rutin (synonym: vitamin P) which reinforces the connective tissue of capillary blood can be used in order to prevent senescence and for reinforcement of blood vessels, chondrithion sulfuric acid (synonym: chondroitin-protein complex) which activates arterial wall cells can be used in arterial sclerosis, particularly in colonary artery sclerosis, also proanthocyanizine which is active in preventing hyperoxidation of lipid and in eliminating active oxygen can be used. As nutritional supplements, vitamins such as vitamin A, $B_1$, $B_2$, $B_6$, $B_{12}$, E, C, niacin and folic acid can be added. Furthermore, zinc, iron, calcium and other nutrients essential for health maintenance of human body can be added.

As aforementioned, powdered vegetable juice according to the present invention is safe to human body and exhibits the health maintenance function existing in vegetables when used not only as beverage also as infant foods and hospital diet after dissolved in water because powdered vegetable juice is constituted with vegetables after nitrate nitrogen harmful to human body were eliminated.

Further, because components effective for healthy life such as blood vessel reinforcers and various vitamins are added, powdered vegetable juice according to the present invention provides various effects good for prevention of blood vessel senescence, for example elimination of active oxygen, improved blood circulation, prevention of senescence of blood vessels due to increase of hyperoxidized lipid, enhancement of capillary blood vessels, decrease of serum cholesterol and the like. Powdered vegetable juice according to the present invention also provides reinforcement effect of blood vessels and tissue cells.

I claim:

1. A powdered vegetable and/or fruit juice, comprising powdered vegetables and/or fruit that are free from nitrate nitrogen and supplemented with blood vessel reinforcers selected from the group consisting of rutin, chondrithion sulfuric acid and proanthocyanizine.

2. The powdered vegetable and/or fruit juice of claim 1, further comprising nutritional supplements selected from the group consisting of vitamins A, $B_1$, $B_2$, $B_6$, $B_{12}$, E, C, niacin, folic acid, zinc, iron and calcium.

3. A process of manufacturing powdered vegetable and/or fruit juice, comprising the steps of:

washing the vegetables and/or fruit with water that has been passed through ion-exchange resins capable of removing $NO_3-$ and $NO_2-$ ions, freeze drying the vegetable and/or fruit;

pulverizing the vegetable and/or fruit; and adding blood vessel reinforcers and nutritional supplements to the pulverized vegetable and/or fruit wherein the blood vessel reinforcers are selected from the group consisting of rutin, chondrithion sulfuric acid and proanthocyanizine: and wherein the nutritional supplements are selected from the group consisting of vitamins A, $B_1$, $B_2$, $B_6$, $B_{12}$, E, C, niacin, folic acid, zinc, iron and calcium.

4. A process of manufacturing powdered vegetable and/or fruit juice as set forth in claim 3, further comprising the step of finely cutting the vegetables and/or fruit to prepare are macerated vegetables and/or fruit prior to washing the vegetables and/or fruit.

5. A juice prepared from a powdered vegetable and/or fruit juice composition, comprising powdered vegetables and/or fruit that are free from nitrate nitrogen and supplemented with blood vessel reinforcers selected from the group consisting of rutin, chondrithion sulfuric acid and proanthocyanizine.

6. The juice of claim 5, further comprising nutritional supplements selected from the group consisting of vitamins A, $B_1$, $B_2$, $B_6$, $B_{12}$, E, C, niacin, folic acid, zinc, iron and calcium.

7. A powder for preparing a juice, the powder comprising: powdered vegetables and/or fruit that are free from nitrate nitrogen and supplemented with blood vessel reinforcers selected from the group consisting of rutin, chondrithion sulfuric acid and proanthocyanizine.

8. The powder of claim 7, wherein the powder is further supplemented with nutritional supplements selected from the group consisting of vitamins A, $B_1$, $B_2$, $B_6$, $B_{12}$, E, C, niacin, folic acid, zinc, iron and calcium.

9. A process of manufacturing powdered vegetable and/or fruit juice, comprising the steps of:

washing the vegetables and/or fruit with water that has been passed through ion-exchange resins capable of removing $NO_3-$ and $NO_2-$ ions;

freeze-drying the vegetable and/or fruit;

pulverizing the vegetable and/or fruit; and adding blood vessel reinforcers to the pulverized vegetable and/or fruit, wherein the blood vessel reinforcers are selected from the group consisting of rutin, chondrithion sulfuric acid and proanthocyanizine.

* * * * *